United States Patent [19]
Schäfer et al.

[11] Patent Number: 4,749,177
[45] Date of Patent: Jun. 7, 1988

[54] PATIENT SUPPORTING TABLE

[75] Inventors: Willi Schäfer; Karl Uebelacker, both of Erlangen, Fed. Rep. of Germany

[73] Assignee: Siemens Aktiengesellschaft, Berlin and Munich, Fed. Rep. of Germany

[21] Appl. No.: 26,003

[22] Filed: Mar. 16, 1987

[30] Foreign Application Priority Data

Mar. 20, 1986 [DE] Fed. Rep. of Germany ... 8607732[U]

[51] Int. Cl.$^4$ ............................................. A61G 13/00
[52] U.S. Cl. ..................................................... 269/323
[58] Field of Search .............................. 269/323–325; 5/62, 66–69; 108/6, 138, 147

[56] References Cited

U.S. PATENT DOCUMENTS

| | | |
|---|---|---|
| 1,656,760 | 1/1928 | Schramm . |
| 1,854,296 | 4/1932 | Emmert ............................... 269/323 |
| 2,217,783 | 10/1940 | Bell ....................................... 269/325 |
| 3,640,520 | 2/1972 | Wieland et al. ..................... 269/323 |
| 3,845,946 | 11/1974 | Warden et al. ...................... 269/323 |
| 3,868,103 | 2/1975 | Pageot et al. ....................... 269/325 |
| 4,045,078 | 8/1977 | Shine .................................... 269/324 |
| 4,059,235 | 11/1977 | Perold ................................. 269/323 |
| 4,333,637 | 6/1982 | Shelton . |

OTHER PUBLICATIONS

Siemens sales brochure "KOORDINAT 3D II" pp. 1–6.

Primary Examiner—Robert C. Watson
Attorney, Agent, or Firm—Hill, Van Santen, Steadman & Simpson

[57] ABSTRACT

A patient supporting table comprises a table top detachably mounted on one side in a cantilevered fashion to an upper part of an height-adjustable pedestal. The upper part is connected to the upper member of a telescoping column by a pivotal connection which allows pivoting around a horizontal shaft which lies close to one edge of the column and preferably at the foot end of the table. This pivotal movement allows easy access to the interior of the pedestal for servicing purposes.

4 Claims, 1 Drawing Sheet

PATIENT SUPPORTING TABLE

BACKGROUND OF THE INVENTION

The present invention is directed to a patient supporting table having a table top which is detachably connected in a cantilever fashion to an upper part of a height-adjustable pedestal.

A patient supporting table is known wherein a thin table top composed of a carbon fiber material is mounted on a pedestal in a cantilevered fashion, and this pedestal is suspended as a column from a ceiling of the examination room. Good access to the patient is thus possible. However, the connection of the table top to the ceiling of the examination room via a column means a great cost for a supporting structure. In addition, the ceilings are not always suitable for the suspension of the patient supporting table.

SUMMARY OF THE INVENTION

The object of the present invention is to provide a patient supporting table having a table top detachably mounted at one side or end in a cantilevered fashion on an upper part of a height-adjustable pedestal which is mounted on the floor and the construction of the pedestal and table is such to provide easy access to parts inside of the pedestal.

These objects are achieved in an improvement of a patient supporting table having a table top detachably connected at one side or end in a cantilevered fashion to an upper part of a height-adjustable pedestal. The improvements are that the height-adjustable pedestal has an upper telescopic column member, and means for connecting the upper part to the telescopic column member adjacent one edge for pivotable movement around a horizontal shaft adjacent said one edge.

The mechanism for the height adjustment, therefore, lies on the inside of the telescopic column member and is easily accessible for maintenance purposes by tilting the upper part around the connecting means.

The other advantages and features of the invention will be readily apparent from the detailed description, drawings and claims.

DESCRIPTION OF THE PREFERRED EMBODIMENTS

Figure 1:
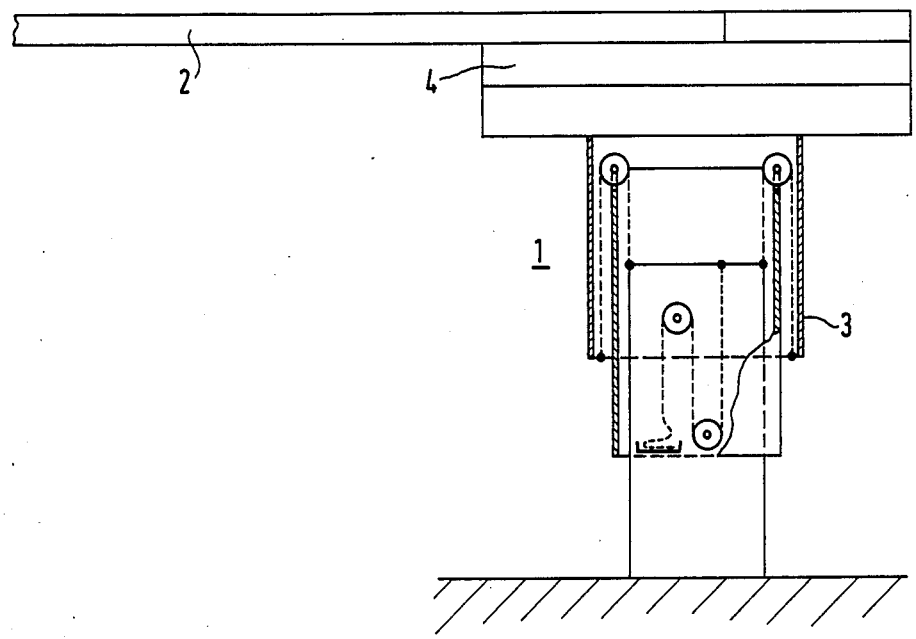
FIG. 1 is a side view with portions broken away for purposes of illustration of a supporting table in accordance with the present invention.

The principals of the present invention are particularly useful in a patient support table illustrated in FIG. 1, which includes a pedestal 1 on which a table top 2 is held at one end in a cantilevered fashion. The pedestal 1 comprises a telescoping column having an upper telescoping column member or part 3. The telescoping column can be raised and lowered by a conventional known mechanism, such as a motor-driven chain hoist which is schematically illustrated in FIG. 1. The table top 2 is connected to the pedestal by means of an upper part 4 which is secured on the upper column member 3. The table top 2 can be detached from the upper part to allow servicing and also for replacement.

Figure 2:
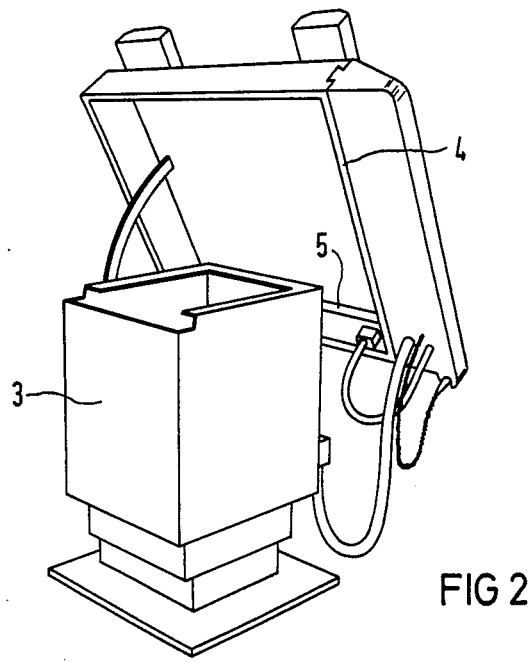
FIG. 2 is a perspective view of the pedestal and upper part with the upper part in an opened position.

As illustrated in FIG. 2, the table top 2 has been removed and the upper part 4 is moved to an opened position. The upper part 4 is connected to the telescoping upper column member 3 by a connection means which enables pivoting around a horizontal shaft 5 which extends close to a foot end of the patient support table. For servicing purposes, accordingly, the table top 2 can be removed and the upper part 4 can be pivoted into the position shown in FIG. 2 so that the inside of the telescoping column is easily accessible. Thus, maintenance jobs on the inside of the telescoping column, for example on the height-adjustment mechanism of the support table, are possible in a simple way without involving the removal of any facing members.

Although various minor modifications may be suggested by those versed in the art, it should be understood that we wish to employ within the scope of the patent granted hereon, all such modifications as reasonably and properly come within the scope of our contribution to the art.

We claim:

1. In a patient supporting table comprising a table top detachably secured at one side in a cantilevered fashion to an upper part of a height-adjustable pedestal, the improvements comprising said height adjustable pedestal having a telescopic column with an upper telescopic column member and further having a height-adjusting mechanism inside said telescopic column, and means for connecting the upper part to the telescopic column for pivotal movement around a horizontal shaft lying close to one edge of said upper telescopic column member, so that said height-adjusting mechanism is accessible by pivoting the upper part on the pedestal.

2. In a patient supporting table according to claim 1, wherein the table top is connected at a foot end to the upper part and the horizontal shaft is positioned at the foot end of said table top.

3. A patient supporting table comprising an upper part, a table top detachably secured at one side in a cantilevered fashion to said upper part, and a height-adjustable pedestal having a telescopic column with an upper telescopic column member and a height-adjusting mechanism inside said telescopic column, said height-adjustable pedestal having means for connecting the upper part to the telescopic column for pivotal movement around a horizontal shaft lying close to one edge of said upper telescopic column member, so that said height-adjusting mechanism in said telescopic column is accessible by pivoting the upper part of the pedestal on said means for connecting.

4. A patient supporting table according to claim 2, wherein the table top is connected at a foot end to the upper part and the horizontal shaft is positioned at the foot end of said table top.

* * * * *